United States Patent [19]

Dye

[11] Patent Number: 4,631,056
[45] Date of Patent: Dec. 23, 1986

[54] TAMPER DISCOURAGING SYSTEM

[75] Inventor: John F. Dye, Elgin, Ill.

[73] Assignee: The Kendall Company, Boston, Mass.

[21] Appl. No.: 630,174

[22] Filed: Jul. 12, 1984

[51] Int. Cl.$^4$ .............................................. A61M 5/00
[52] U.S. Cl. .................................... 604/111; 604/905; 285/3
[58] Field of Search .................... 604/110–111, 604/905, 283, 165, 86, 411, 414; 285/3

[56] References Cited

U.S. PATENT DOCUMENTS

| | | | |
|---|---|---|---|
| 4,013,064 | 3/1977 | Patel et al. | 604/86 |
| 4,116,227 | 9/1978 | Eisenberg et al. | 604/86 |
| 4,194,509 | 3/1980 | Pickering et al. | 604/111 |
| 4,286,640 | 9/1981 | Knox et al. | 604/111 |
| 4,326,516 | 4/1982 | Schultz et al. | 604/283 |
| 4,340,052 | 7/1982 | Dennehey et al. | 604/905 |
| 4,405,312 | 9/1983 | Gross et al. | 604/283 |
| 4,432,767 | 2/1984 | Lobdell et al. | 604/86 |

Primary Examiner—John D. Yasko
Assistant Examiner—Gene B. Kartchner
Attorney, Agent, or Firm—Powell L. Sprunger

[57] ABSTRACT

A tamper discouraging system comprising, a catheter having an elongated shaft and a hollow connector at a proximal end of the shaft. The system has a drainage tube having an adapter at an upstream end of the drainage tube, with the adapter being received in the connector. The system has a first semi-annular shell for placement over the connector, and a second semi-annular shell for placement over the connector. The system has a hinge connecting one end of the first shell to one end of the second shell, and a locking device for locking the other end of the first shell to the other end of the second shell.

8 Claims, 7 Drawing Figures

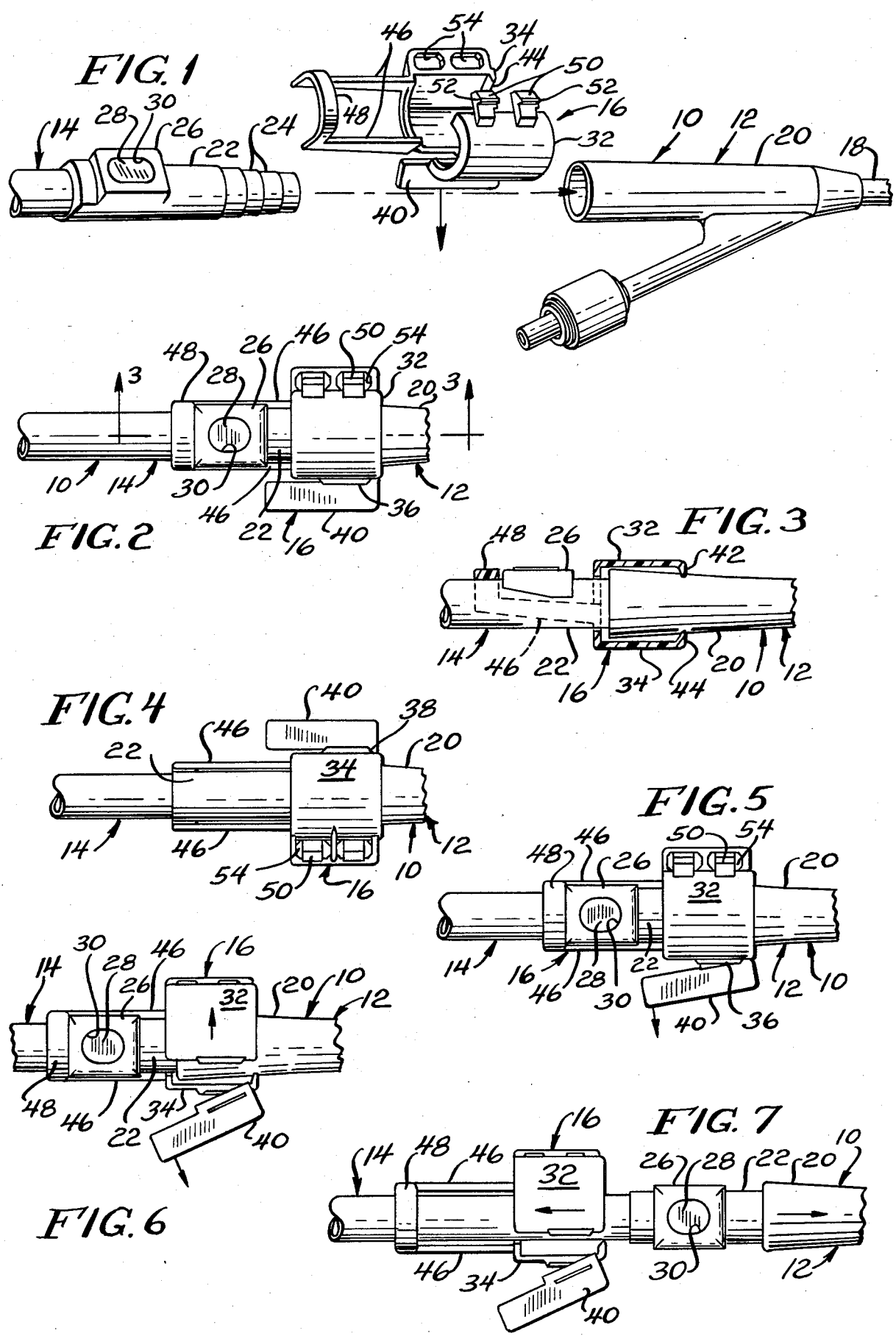

TAMPER DISCOURAGING SYSTEM

BACKGROUND OF THE INVENTION

The present invention relates to liquid drainage systems.

Liquid drainage systems of the type which drain urine from a patient's bladder are known. Such systems generally comprise a catheter having a distal end received in the patient's bladder and a drainage lumen extending through the catheter, a hollow drainage tube, and a collection bag connected to a downstream end of the drainage tube, with an adapter at an upstream end of the drainage tube being received in a connector adjacent a proximal end of the catheter. In use, urine drains from the bladder through the catheter and drainage tube into the collection bag for collection therein.

Such drainage systems are sterile and are closed to the atmosphere to prevent bacteria from entering the system which otherwise might pass by retrograde movement into the bladder with possible deleterious results to the patient. In particular, it is undesirable to remove the adapter from the catheter connector since such a procedure could allow entry of bacteria into the system. Hence, it is desirable to discourage such disconnection, and, at the very least, if it is necessary to make the disconnection, such as for irrigation of the catheter, it is desirable to know when such a disconnection has taken place.

SUMMARY OF THE INVENTION

A principal feature of the present invention is the provision of an improved liquid drainage system.

In accordance with the present invention the liquid drainage system has a tamper discouraging system comprising, a catheter having an elongated shaft and a hollow connector at a proximal end of the shaft. The system has a drainage tube having an adapter at an upstream end of the drainage tube, with the adapter being received in the connector. The system has a first semi-annular shell for placement over the connector, and a second semi-annular shell for placement over the connector. The system has hinge means connecting one end of the first shell to one end of the second shell, and means for locking the other end of the first shell to the other end of the second shell.

A feature of the present invention is that the shells discourage removal of the adapter from the catheter connector.

Another feature of the invention is that the shells include means for gripping the catheter.

A further feature of the invention is the provision of a tab adjacent the hinge means for rupturing the shells from each other.

Another feature of the invention is that the ruptured shells indicate when the adaptor may have been removed from the catheter connector.

A feature of the present invention is the provision of means for locking the adapter to the connector.

Further features will become more fully apparent in the following description of the embodiments of this invention and from the appended claims.

DESCRIPTION OF THE DRAWINGS

In the drawings:

FIG. 1 is an exploded perspective view of a tamper discouraging system of the present invention;

FIG. 2 is a fragmentary top plan view of the system of FIG. 1;

FIG. 3 is a fragmentary elevational view, taken partly in section, along the line 3—3 of FIG. 2;

FIG. 4 is a fragmentary bottom plan view of the system of FIG. 1;

FIGS. 5 and 6 are fragmentary top plan views illustrating the rupturing of a tamper discouraging device in the system; and FIG. 7 is a fragmentary top plan view illustrating the device as being slid down a drainage tube.

DESCRIPTION OF THE PREFERRED EMBODIMENTS

Referring now to FIGS. 1–4, there is shown a tamper discouraging system generally designated 10 having a catheter 12, a drainage tube 14, and a tamper discouraging device 16. The catheter 12 has an elongated shaft 18, and a hollow connector 20 connected to a proximal end of the shaft 18.

The drainage tube 14 has an adapter 22 secured to an upstream end of the drainage tube 14. As shown, the upstream end of the adapter 22 is tapered in a suitable manner, such as by steps 24. The adapter 22 also has an upstanding member 26 with an elastic plug 28 received in an opening 30 of the member 26. The plug 28 serves as a sampling port such that a needle may be passed through the plug 28 in order to obtain a sample of urine passing through the system. In use of the system 10, the adapter 22 is received in the catheter connector 20.

The device 16 has a first semi-annular shell 32 for placement over the connector 20, and a second semi-annular shell 34 for placement over the connector 20. The device 16 has a pair of spaced longitudinally extending weakness lines 36 and 38 at one end of the shells 32 and 34 which serve as a hinge such that the shells 32 and 34 may be open, as shown in FIG. 1, or closed about the connector 20 as shown in FIGS. 2–4. The device 16 has an outwardly directed tab 40 intermediate the weakness lines 36 and 38 for a purpose which will be described below. The shells 32 and 34 have distal inwardly directed flanges 42 and 44 for a purpose which will be described below. The shell 34 has a pair of proximally directed arms 46 and an arcuate flange 48 connecting a proximal end of the arms 46. The shell 32 has a pair of outwardly directed tabs 50 at the other end of the shell 32, with the tabs 50 each having an outwardly directed boss 52. The shell 34 has a pair of openings 54 at the other end of the shell 34, with the openings 54 being aligned with the tabs 50.

In use, after placement of the adapter 22 in the connector 20, the shells 32 and 34 are placed over the connector 20 in the open position, as shown in FIG. 1. Next, the shells 32 and 34 are squeezed toward each other until the tabs 50 are received in the openings 54 after which the bosses 52 engage the shell 34 around the openings 54 in order to securely lock the other end of the shells 32 and 34 together over the connector 20. In this configuration, as shown in FIG. 3, the flanges 42 and 44 securely grip against the outer surface of the connector 20 in order to prevent movement of the device 16 along the connector 20. Also, in this configuration, the flange 48 is received against a proximal side of the member 26 in order to lock the drainage tube 14 to the catheter 12. Thus, in this configuration, the tamper discouraging device 16 prevents removal of the adapter 22 from the catheter connector 20.

In the event that it is desired to remove the adapter 22 from the connector 20, such as for irrigation of the catheter, the tab 40 is either pulled outwardly or twisted in order to rupture the weakness lines 36 and 38 and sever the shells 32 and 34 from each other, as shown in FIGS. 5 and 6. At this time, if desired, the device 16 may be removed from the catheter 12 and drainage tube 14 and may be discarded. Alternatively, as shown in FIG. 7, the ruptured device 16 may be slid down the drainage tube 14 toward a downstream end of the drainage tube 14. In either event, the absence of the device 16 or the placement of the device 16 toward the downstream end of the drainage tube indicates that the adapter 22 has been removed from the connector 20.

Thus, in accordance with the present invention, a tamper discouraging device 16 is provided in order to lock a drainage tube adapter 22 into a catheter connector 20 in order to discourage removal of the adapter 22 from the connector 20. However, in the event that it is necessary to remove the adapter 22 from the connector 20, the device 16 may be ruptured, and the subsequent removal of the device 16 from the catheter 12 and drainage tube 14 indicates that the adapter 22 has been removed from the catheter connector 20.

The foregoing detailed description is given for clearness of understanding only, and no unnecessary limitations should be understood therefrom, as modifications will be obvious to those skilled in the art.

I claim:
1. A tamper discouraging system, comprising:
   a catheter having an elongated shaft and a hollow connector at a proximal end of the shaft;
   a drainage tube having an adapter at an upstream end of the drainage tube, with said adapter being received in the connector;
   a first semi-annular shell for placement over the connector;
   a second semi-annular shell for placement over the connector;
   hinge means connecting one end of the first shell to one end of the second shell; and
   means for locking the other end of the first shell to the other end of the second shell, wherein the hinge means comprises a spaced pair of lines of weakness adjacent the one end of the first and second shells, and including an outwardly directed tab intermediate the lines of weakness to rupture the hinge means.
2. The system of claim 1 wherein said first and second shells include means for gripping the catheter.
3. The system of claim 2 wherein the gripping means comprises inwardly directed flanges on a distal end of the first and second shells.
4. The system of claim 1 wherein the hinge means comprises a line of weakness adjacent the one end of the shells.
5. The system of claim 1 wherein the locking means comprises at least one tab adjacent the other end of one shell, and an opening adjacent the other end of the other shell to receive the tab.
6. The system of claim 5 wherein said tab includes an outwardly directed boss to securely lock the tab in the opening.
7. The system of claim 1 wherein said adapter includes an upstanding member, and in which one of said shells includes a pair of proximately directed arms and an arcuate flange connecting a proximal end of the arms, said flange being placed against a proximal end of said member.
8. The system of claim 7 wherein said member comprises a sampling port.

* * * * *